(12) United States Patent
Chen

(10) Patent No.: US 12,132,399 B2
(45) Date of Patent: Oct. 29, 2024

(54) DC POWER SUPPLY UNIT FOR A TATTOO MACHINE AND CAPABLE OF OUTPUTTING SQUARE WAVES

(71) Applicant: Ching-Hsiang Chen, Tainan (TW)

(72) Inventor: Ching-Hsiang Chen, Tainan (TW)

( * ) Notice: Subject to any disclaimer, the term of this patent is extended or adjusted under 35 U.S.C. 154(b) by 1163 days.

(21) Appl. No.: 16/879,140

(22) Filed: May 20, 2020

(65) Prior Publication Data
US 2020/0376248 A1   Dec. 3, 2020

(30) Foreign Application Priority Data
May 30, 2019  (TW) .................................. 108118732

(51) Int. Cl.
*H02M 3/00*     (2006.01)
*A61M 37/00*    (2006.01)

(52) U.S. Cl.
CPC .......... *H02M 3/00* (2013.01); *A61M 37/0076* (2013.01); *A61M 2205/10* (2013.01); *A61M 2205/502* (2013.01)

(58) Field of Classification Search
CPC ................ H02M 3/00; A61M 37/0076; A61M 2205/10; A61M 2205/502
USPC ......................................................... 327/291
See application file for complete search history.

(56) References Cited

U.S. PATENT DOCUMENTS

| | | | | |
|---|---|---|---|---|
| 10,687,652 | B1* | 6/2020 | Kwiatkowski | A47J 31/10 |
| 10,971,991 | B2* | 4/2021 | Kato | H02M 7/53871 |
| 2010/0241151 | A1* | 9/2010 | Rickard | A61M 37/0076 606/186 |
| 2013/0099709 | A1* | 4/2013 | Tsai | H02P 7/29 318/434 |
| 2014/0313786 | A1* | 10/2014 | Chen | H02M 1/4266 363/21.01 |
| 2020/0204057 | A1* | 6/2020 | Kato | H02M 7/53871 |
| 2020/0376248 | A1* | 12/2020 | Chen | A61M 37/0076 |
| 2021/0060325 | A1* | 3/2021 | Xiao | G10L 15/00 |
| 2023/0283172 | A1* | 9/2023 | Gao | H02M 1/42 363/21.02 |
| 2023/0412050 | A1* | 12/2023 | Anderson | H02P 6/16 |

* cited by examiner

*Primary Examiner* — Ryan Jager
(74) *Attorney, Agent, or Firm* — Rosenberg, Klein & Lee

(57) ABSTRACT

A power supply unit for a tattoo machine includes a power operating unit electrically connected to a power supply device. The power operating unit is electrically connected to an operating unit. The power operating unit can output a DC power and can control a current value or a voltage value of the DC power according to operation of the operating unit. A modulating unit is electrically connected to the power operating unit and the operating unit. The modulating unit modulates the DC power according to the operation of the operating unit and outputs a square wave power or the DC power. The modulating unit can control frequency or a work cycle of the square wave power according to the operation of the operating unit. An output end of the DC power supply unit is electrically connected to the tattoo machine to output the square wave power or the DC power.

4 Claims, 1 Drawing Sheet

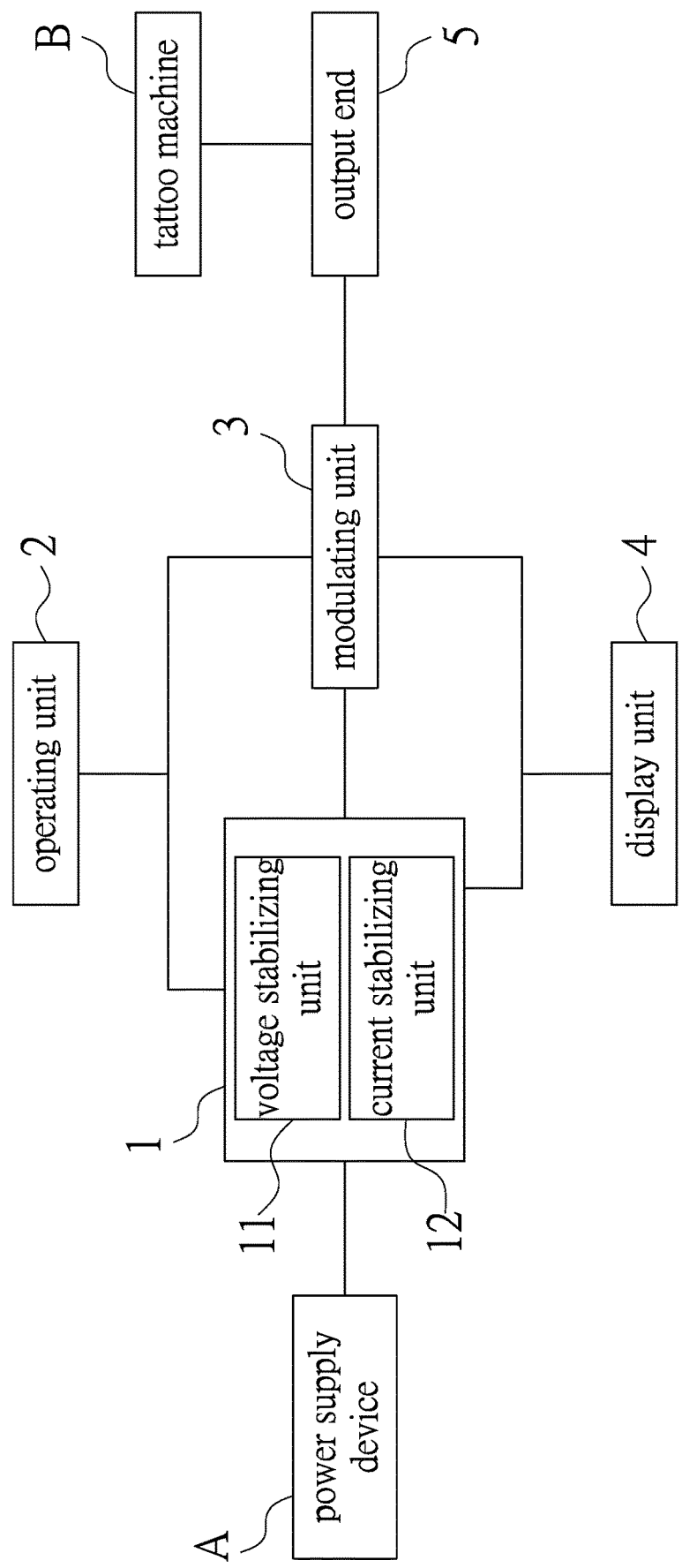

DC POWER SUPPLY UNIT FOR A TATTOO MACHINE AND CAPABLE OF OUTPUTTING SQUARE WAVES

BACKGROUND OF THE INVENTION

The present invention relates to a DC power supply unit and, more particularly, to a DC power supply unit for a tattoo machine and capable of outputting square waves.

The ethos of the early Taiwan society was conservative, and most people had a negative feeling about tattoo. With years of propagation and marketing by tattoo fans, tattoo has gradually been given values of fashion, or showing self-characteristics, or memory, reversing the adverse feeling of people.

Typical tattoo tools include a tattoo machine, a pedal switch, and a power supply. The pedal switch can be pedaled to control whether to supply electricity from the power supply to the tattoo machine. The power supply mainly supplies a stable voltage to the tattoo machine. The tattoo machine includes a needle that repeatedly punctures the human skin to allow the pigments to enter the human skin. To achieve repeated downward movement of the needle, the tattoo machines generally include a motor type and a coil type. A motor-type tattoo machine uses a motor as a power system for reciprocatingly moving the needle. A coil-type tattoo machine uses a relay as a core, and the needle is driven to reciprocate upon activation and deactivation of the relay. Activation or deactivation of the relay is controlled by a mechanical approach or a non-mechanical approach. The mechanical approach uses the characteristics of the relay and the structural arrangement to provide automatic cycles of power on, power off, and power on after the tattoo machine is powered, thereby reciprocatingly moving the needle, and a mechanical tattoo machine referred to hereinafter adopts the mechanical approach. The non-mechanical approach supplies square waves to the tattoo machine to provide automatic cycles of power on, power off, and power on, thereby reciprocatingly moving the needle, and a non-mechanical tattoo machine referred to hereinafter adopts the non-mechanical approach.

Most of the tattoo machines are of mechanical type in the past 100 years, such that selection of the power supply generally focuses on the voltage stabilizer providing direct current. Since this power supply continuously providing direct current cannot provide square waves, this power supply cannot be used in non-mechanical tattoo machines, leading to limited applications. Furthermore, in use of this power supply providing a stable voltage only, the needle cannot smoothly penetrate the epidermis or dermis of a client having a stiffer skin, failing to provide a good tattoo effect. On the other hand, when the client has a softer skin, the needle penetrates too deep, which also adversely affects the tattoo effect.

Thus, a need exists for a novel power supply for supplying a stable voltage, a stable current and square waves to the tattoo machine to thereby solve the above disadvantages while allowing a smoother tattoo procedure.

BRIEF SUMMARY OF THE INVENTION

In view of the disadvantages of the prior art, the present invention provides a power supply unit for a tattoo machine and capable of outputting square waves. The power supply unit comprises:

a power operating unit configured to be electrically connected to a power supply device, wherein the power operating unit is electrically connected to an operating unit, wherein the power operating unit is configured to output a DC power and to control a current value or a voltage value of the DC power according to operation of the operating unit;

a modulating unit electrically connected to the power operating unit and the operating unit, wherein the modulating unit is configured to determine whether to modulate the DC power according to the operation of the operating unit and outputs a square wave power or the DC power, wherein the modulating unit is configured to control frequency or a work cycle of the square wave power according to the operation of the operating unit; and an output end configured to be electrically connected to the tattoo machine to output the square wave power or the DC power.

In an example, the power operating unit includes a voltage stabilizing unit electrically connected to the operating unit and a current stabilizing unit electrically connected to the operating unit. The voltage stabilizing unit controls the voltage value of the DC power according to the operation of the operating unit. The current stabilizing unit controls the current value of the DC power according to the operation of the operating unit.

In an example, the DC power supply unit further comprises a display unit electrically connected to the power operating unit and the modulating unit. The display unit is configured to display the current value, the voltage value, the work cycle, and the frequency.

Thus, the DC power supply unit designed by the Applicant can be used on a tattoo machine and can output square waves. When the DC power supply unit according to the present invention is used on a mechanical tattoo machine, the work cycle can be set to 1 through operation of the operating unit, permitting electricity to be supplied to the mechanical tattoo machine. Even if the work cycle is not set to 1, activation of the mechanical tattoo machine is not affected. When the DC power supply unit according to the present invention is used on a non-mechanical tattoo machine, the work cycle can be adjusted according to needs. Generally, the work cycle is preferably set to 0.5. Thus, the characteristics of the square waves can be used to control operation of the non-mechanical tattoo machine.

Furthermore, the operating unit can be operated to control output of the voltage value or the current value. In a case that a client has a stiffer skin, the current value is increased to provide the tattoo machine with a larger output force to penetrate the skin. In another case that the client has a softer skin, the current value is reduced. Thus, the present invention can be widely used on clients with different skin statuses, allowing an easier tattoo process. Thus, the present invention provides functions of outputting square waves, controlling the current value, etc. This is a breakthrough in the tattoo field and reverses the bias against the power supply unit which can only supply a stable voltage. Accordingly, the present invention is easier to use and provides wider applications.

The present invention will become clearer in light of the following detailed description of illustrative embodiments of this invention described in connection with the drawings.

DESCRIPTION OF THE DRAWINGS

The FIGURE is a diagrammatic view illustrating connections of components of a DC power supply unit of an embodiment according to the present invention.

DETAILED DESCRIPTION OF THE INVENTION

With reference to the FIG., a DC power supply unit for a tattoo machine B and capable of outputting square waves of an embodiment according to the present invention comprises a power operating unit 1, a modulating unit 3, and an output end 5. The power operating unit 1 is configured to be electrically connected to a power supply device A, such as a commercial power. Furthermore, the power operating unit 1 is electrically connected to an operating unit 2. The power operating unit 1 is configured to output a DC power and to control a current value or a voltage value of the DC power according to operation of the operating unit 2.

The operating unit 2 is configured to be operated by a user to control various parameters, such as the work cycle, current value, voltage value, frequency, etc. of the tattoo machine. In practice, the operating unit 2 can be a plurality of knobs or buttons. Furthermore, to provide a stable power to the tattoo machine, the power operating unit 1 preferably includes a voltage stabilizing unit 11 electrically connected to the operating unit 2 and a current stabilizing unit 12 electrically connected to the operating unit 2. The voltage stabilizing unit 11 can control the voltage value of the DC power according to the operation of the operating unit 2. The current stabilizing unit 12 can control the current value of the DC power according to the operation of the operating unit 2.

With reference to the FIG., the modulating unit 3 is electrically connected to the power operating unit 1 and the operating unit 2. The modulating unit 3 is configured to determine whether to modulate the DC power according to the operation of the operating unit 2 and outputs a square wave power or the DC power. The modulating unit 3 is configured to control frequency or a work cycle of the square wave power according to the operation of the operating unit 2.

With reference to the FIGURE, the DC power supply further comprises a display unit 4 electrically connected to the power operating unit 1 and the modulating unit 3. The display unit 4 is configured to display the current value, the voltage value, the work cycle, and the frequency. With reference to the FIGURE, the output end 5 is configured to be electrically connected to the tattoo machine B to output the square wave power or the DC power.

The present invention is intended to overcome the bias against the power supply for tattoo machines. Since mechanical tattoo machines are the mainstream of the tattoo machines in many years, the power supply can be readily used for the tattoo machines without outputting square waves. However, this also causes limitation of the power supply in application on non-mechanical tattoo machines, resulting in limited use.

In view of the foregoing, through cooperation of the operating unit 2 and the modulating unit 3, the DC power supply unit according to the present invention can output the square wave power or the DC power according to the type of the tattoo machine. When used on a non-mechanical tattoo machine, the modulating unit 3 outputs the square wave power after operation, such that the non-mechanical tattoo machine can control reciprocating movement of a needle thereof by using the characteristics of the square waves. When used on a mechanical tattoo machine, either the square wave power or the DC power is outputted although the DC power is preferred. Furthermore, a user can decide the work cycle and frequency of the square wave power through the operating unit 2. In an example, the work cycle is preferably 0.5. In a case that the user decides to output the DC power, the work cycle is set to 1.

Furthermore, through cooperation of the operating unit 2 and the power operating unit 1, the current value or the voltage value of the square wave power or the DC power can be varied according to different conditions. For example, in a case that a client has a stiffer skin, the current value is increased to provide the tattoo machine B with a larger output force, and the needle can stably penetrate the skin to a depth of 0.2 mm. In another case that the client has a softer skin, the current value is reduced to reduce the output force of the tattoo machine B, avoiding excessive penetration of the needle. Furthermore, due to the characteristics of the current stabilizing unit 12, a fixed current can be stably outputted. Thus, the output force of the tattoo machine B is fixed regardless of the conditions encountered. When it is desired to fix the output power, the voltage stabilizing unit 11 can be used for modulation.

Since use of conventional mechanical tattoo machines highly rely on the experience and the sense of the tattoo mentor using the tattoo machine, the legacy of the tattoo art and technical exchange between tattoo mentors are greatly restricted. For example, a tattooist generally rotates a rod on a mechanical tattoo machine to adjust the work cycle or frequency of the tattoo machine. However, the adjustment greatly relies on the personal feeling and is difficult to objectify, concretize, and digitize, requiring a long period of time in learning and operation. Furthermore, adjustment of the work cycle or frequency of a mechanical tattoo machine is relatively complicated. Aside from adjustment of the rod that affects the work cycle, a touch or impact on a front resilient plate, a rear resilient plate, or a suspended iron of the mechanical tattoo machine or an external impact to the mechanical tattoo machine (such as falling onto the ground) could significantly change the work cycle. These further increase the difficulties in learning the tattoo art and requiring additional time and energy for adjusting the tool during work.

The present invention addresses the above problems and have several advantages. Regardless of the type of the tattoo machine, the display unit 4 can display various parameters, such as the work cycle, frequency, current value, voltage value, etc. Thus, when a tattoo mentor intends to teach an apprentice, these parameters can be digitalized to guide the apprentice how to operate or how to set these parameters during various line cutting and fogging procedures. Furthermore, extensively laborious adjustment of the work cycle of the tattoo machine is not required, the effect of which is more obvious when used on a non-mechanical tattoo machine. Furthermore, when a tattoo mentor has developed a special technique, this technique can be concretized and digitalized through various parameters to permit more efficient technical communication without relying on conventional communication or guiding based on "feeling". Thus, the technical communication or legacy of the tattoo art is more efficient and concrete.

Although specific embodiments have been illustrated and described, numerous modifications and variations are still possible without departing from the scope of the invention. The scope of the invention is limited by the accompanying claims.

What is claimed is:

1. A DC power supply unit for a tattoo machine and capable of outputting square waves, comprising:
   a power operating unit configured to be electrically connected to a power supply device, wherein the power operating unit is electrically connected to an operating unit, wherein the power operating unit is configured to output a DC power and to control a current value or a voltage value of the DC power according to operation of the operating unit;

a modulating unit electrically connected to the power operating unit and the operating unit, wherein the modulating unit is configured to determine whether to modulate the DC power according to the operation of the operating unit and outputs a square wave power or the DC power, wherein the modulating unit is configured to control frequency or a work cycle of the square wave power according to the operation of the operating unit; and an output end configured to be electrically connected to the tattoo machine to output the square wave power or the DC power.

2. The DC power supply unit for the tattoo machine and capable of outputting square waves as claimed in claim 1, wherein the power operating unit includes a voltage stabilizing unit electrically connected to the operating unit and a current stabilizing unit electrically connected to the operating unit, wherein the voltage stabilizing unit controls the voltage value of the DC power according to the operation of the operating unit, and wherein the current stabilizing unit controls the current value of the DC power according to the operation of the operating unit.

3. The DC power supply unit for the tattoo machine and capable of outputting square waves as claimed in claim 2, further comprising a display unit electrically connected to the power operating unit and the modulating unit, and wherein the display unit is configured to display the current value, the voltage value, the work cycle, and the frequency.

4. The DC power supply unit for the tattoo machine and capable of outputting square waves as claimed in claim 1, further comprising a display unit electrically connected to the power operating unit and the modulating unit, and wherein the display unit is configured to display the current value, the voltage value, the work cycle, and the frequency.

* * * * *